United States Patent [19]
Ishida et al.

[11] Patent Number: 6,160,079
[45] Date of Patent: Dec. 12, 2000

[54] ACTIVATED ARYLAMINE-BASED POLYBENZOXAZINES

[75] Inventors: Hatsuo Ishida, Shaker Heights, Ohio; Daniel Sanders, Rochester, Minn.

[73] Assignee: Edison Polymer Innovation Corporation, Akron, Ohio

[21] Appl. No.: 09/291,466

[22] Filed: Apr. 14, 1999

[51] Int. Cl.[7] .............................. C08G 14/06; C08G 8/04
[52] U.S. Cl. ..................... 528/129; 528/137; 528/145; 528/146; 544/69; 544/90
[58] Field of Search .................... 528/129, 137, 528/145, 146; 544/69, 90

[56] References Cited

U.S. PATENT DOCUMENTS

| | | | |
|---|---|---|---|
| 4,501,864 | 2/1985 | Higginbottom et al. | 525/484 |
| 4,507,428 | 3/1985 | Higginbottom et al. | 524/596 |
| 5,543,516 | 8/1996 | Ishida | 544/69 |

*Primary Examiner*—Duc Truong
*Attorney, Agent, or Firm*—Hudak & Shunk Co., L.P.A.

[57] ABSTRACT

Arylamines with electron donating groups such as alkyl and alkoxy groups in the meta position on the aromatic ring change the polymerization temperature of the benzoxazine prepared therefrom and offer an opportunity for an additional crosslinking site (the para position on the aromatic amine can couple to a Mannich base generated by the opening of the oxazine ring of the benzoxazine or a methylene bridge generated by a degradation reaction). Naphthenic amines with an alkyl or alkoxy substituent on the $5^{th}$ through the $8^{th}$ carbon atom on the naphthalene ring can function similarly. The polymers for benzoxazines prepared from at least 10% substituted aromatic or naphthenic amines are useful due to low polymerization temperatures and higher Tg (glass transition temperature).

19 Claims, No Drawings

ACTIVATED ARYLAMINE-BASED POLYBENZOXAZINES

FIELD OF INVENTION

The invention field is benzoxazines. Benzoxazines are an alternative to phenolic, epoxy, and other thermosetting resins in many applications due to their similar thermal stability and the processing advantages of benzoxazines. Benzoxazines offer useful properties including low viscosity, little or no release of volatiles during cure, no need for harsh catalysts, a high glass transition temperature, high thermal stability, -good mechanical properties, and wide molecular design flexibility. Substituted aromatic amines offer an additional site on the aromatic amine to build the polybenzoxazine's molecular weight and/or to provide crosslinking sites. These changes in the polymer should result in better thermal stability over some temperature range and improved physical properties over some temperature range.

BACKGROUND OF INVENTION

The effect of various substituents on the reactivity of aromatic amines in some reactions has been studied. The electronegativity of the substituent and its position (e.g. ortho, meta, and para) on the amine has an effect on the reactivity of the amine in chemical reactions including electrophilic aromatic substitution reactions. One set of papers discussing this is by M. Miocque and J. M. Vierfond in the Bull. Soc. Chim. Fr. (1970), volume 5, pages 1896, 1901, and 1910.

It is known that one of the degradation products of thermal decomposition of aromatic amine containing benzoxazine polymers is the aromatic amine. It has been proposed to add acetylene, phthalonitrile and nitrile functional groups to an aromatic amine to generate an additional chemical bond between the aromatic amine and the rest of the polybenzoxazine network. Conceptually, the added chemical bond would decrease the amount of aromatic amine volatilized thereby increasing the thermal stability of the benzoxazine polymer. This was effective, but the aromatic amines with the acetylene, phthalonitrile and nitrile functional groups are difficult to prepare and significantly raise the product's cost.

SUMMARY OF INVENTION

It has been discovered that aromatic amines with substituents, which activate the ring of the aromatic amine for electrophilic aromatic substitution reactions at the para position, can sufficiently activate the ring so that said para position of the amine competes with the ortho position on the phenolic reactant for chemical reaction with the Mannich bridge formed during the ring opening polymerization of benzoxazine. Naphthenic amines with alkyl and/or alkoxy substituents on the $5^{th}$ through the $8^{th}$ carbon atom of the naphthalene can be substituted for the aromatic amine with similar results. Several of the substituents such as a meta-methyl group also facilitate ring opening of the benzoxazine monomer which is part of the polymerization process for benzoxazines. This may lower the polymerization temperature and provide for higher molecular weight or crosslinked polybenzoxazines.

It is desirable that at least 10 or 25 mole percent and more desirably at least 50 mole percent of the total amines used to form the benzoxazine monomer and benzoxazine polymer are aromatic amines that have substituents that activate the aromatic ring for electrophilic substitution reactions with the Mannich base in the para position. Preferred substituents are electron donating groups such as mono or di-alkyl or mono or di-alkoxy groups in the meta position. The substituted aromatic amine may be partially or fully replaced with a substituted naphthenic amine. Preferred phenolic compounds are mono, di, or polyhydric phenolic molecules which can form one or more benzoxazine rings per phenolic molecule.

DETAILED DESCRIPTION OF THE INVENTION

Polybenzoxazines with improved properties due to the use of a substituted arylamine are described. While the char yield of such polybenzoxazines is not substantially better than similar benzoxazines from aniline, the properties and thermal stability between 200 and 350° C. are improved. It is intended to claim not only the polybenzoxazines but the monomers used to make them and the processes used in their preparation. It is acknowledged that the term polybenzoxazine may be confusing to some because a polybenzoxazine typically has no residual benzoxazine containing repeat units since the benzoxazine ring is opened as part of the polymerization process. A benzoxazine monomer does have at least one benzoxazine ring and may have multiple benzoxazine rings.

Benzoxazine monomers generally have a formula with an oxazine ring pendant to a benzene ring such as shown below

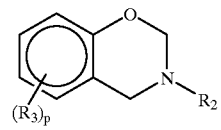

Formula A

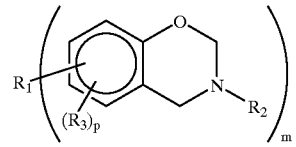

Formula B wherein m can be any integer from 1 to 20 and is preferably an integer from 1 to 4 and is most preferably 2 or 3, and $R_1$ is one of the connecting groups such as shown later for the phenolic molecules. Furthermore, each benzene ring, as shown by $(R_3)_p$ where p is an integer from 0 to 3 and $R_3$ is as defined later, can have one or more substituents of the same structure or a mixture of the $R_3$ structures. Preferably $R_3$ is an alkyl of 1 to 16 carbon atoms such as $CH_3$, $C_2H_5$, $C_3H_7$ or $C_4H_9$, or a mono or poly fluorinated alkyl of 1 to 9 carbon atoms such as $CF_3$, $C_2F_5$, $C_3F_7$. $R_2$ can be anything that when attached to $NH_2$ would generate the amines described later.

Benzoxazines have been shown to polymerize via a thermally induced ring-opening reaction to form a phenolic structure characterized by a Mannich base bridge ($-CH_2-NR_1-CH_2-$) as shown instead of the methylene bridge associated with traditional phenolic resins.

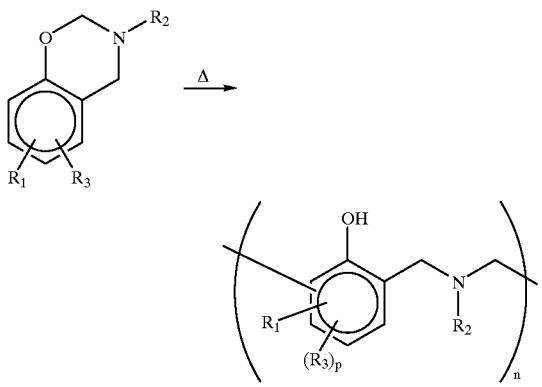

This thermal polymerization typically evolves very small amounts of byproducts because, as the oxazine ring is opened, it attaches to an ortho or para position on another aromatic ring generating a hydrogen from the attachment to the ring, which is available to form the hydroxyl group of a phenol. The major source, if any, of byproducts is side reactions that may cleave the Mannich bridge from the phenol or cleave the Mannich bridge. This can be controlled by choosing proper polymerization conditions. Alternatively the polymerization can be initiated or catalyzed. Cationic ring opening polymerization is taught in U.S. patent application Ser. No. 09/105,859.

Unfortunately with typical monofunctional benzoxazines the polymer molecular weight never gets very high during uncatalyzed thermally initiated polymerization as side reactions and thermal degradation limits the molecular weight. Therefore many polybenzoxazine producers use difunctional or polyfunctional phenols to generate two or more benzoxazine rings on the benzoxazine monomer. Using polyfunctional benzoxazines the molecular weight of the polymer can be significantly increased and crosslinking can be achieved even with significant levels of side reactions and impurities.

Generally an early thermal degradation product, whether during polymerization or post polymerization, is the amine of the Mannich bridge. This is the focus of this disclosure as decreasing the amount of amine generated early in thermal degradation may be the best route to increase the thermal stability of the polybenzoxazine. While the attachment of additional reactive groups, e.g. acetylene, phthalonitrile and nitrile functional groups does decrease the amount of amine released during thermal degradation (low temperature) and also increases the char yield of the polymer at 800° C., this is a costly component to the recipe. An alternative, as explained herein, is to use a reactant that favors additional chemical bonds being formed to the amine component or favors the generation of more thermally stable byproducts early in the polymerization without the use of expensive, reactive substituents attached to the aryl amine such as acetylene, phthalonitrile and/or nitrile.

Amines desirable for forming the benzoxazines are aromatic amines with substituents that favor electrophilic substitution reactions at the para position of the aromatic group. Preferred loci of the substituents are the meta positions on the benzene ring. Preferred meta substituents are alkyls of 1 to 4 carbon atoms or alkoxy groups of 1 to 4 carbon atoms. Highly preferred is meta methyl groups such as found on 3-methyl aniline (3-toluidine) and 3,5-dimethyl aniline (3,5-xylidine) and meta methoxy groups such as found on 3-methoxy aniline. Methyl is an electron donating substituent and activates the para position on the ring for electrophilic substitution. Substituents in the para position are not preferred as it is difficult to form a covalent bond to the arylamine in the ortho or meta positions due to steric hindrance and/or electronic reasons. Substituents in the ortho position are not preferred as they are a steric hindrance and reduce the reactivity of the oxazine ring in the reaction forming the polybenzoxazine.

Alternatively or in combination with the above aromatic amines one can use naphthenic amines with alkyl or alkoxy substituents as described above. The location of the substituents on the naphthenic amines need not be in the meta position but should be on the ring not bonded directly to the nitrogen. Thus on the fused rings below the alkyl and/or alkoxy substituents could be on the $5^{th}$ through $8^{th}$ carbon atom.

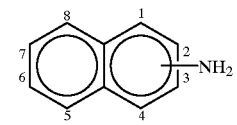

Desirably at least 10 or 25 mole percent and preferably at least 50 mole percent of the amines used to form the benzoxazine or incorporated into the polybenzoxazine are the above described aromatic amines with para directing substituents for electrophilic aromatic substitution reactions and/or said naphthenic amines. In the polybenzoxazine polymer desirably at least 0.01 mole percent, more desirably at least 0.1 mole percent, and preferably at least 0.5 mole percent of the total substituted aromatic amines and naphthenic amines have a Mannich bridge or methylene bridge attached to the aromatic ring thereof.

The benzoxazines containing the above substituted aryl amines can be prepared by mixing the substituted arylamines with other amines and then making the benzoxazines therefrom or benzoxazines prepared primarily or entirely of said substituted arylamines can be copolymerized with other benzoxazines containing said other amines, e.g. an aromatic amine, aliphatic amine, alkyl substituted aromatic or aromatic substituted alkyl amine, halogenated aliphatic amine, or halogenated aromatic amine or combinations thereof. The amine can also be a polyamine, although the use of polyamines will, under some circumstances, yield polyfunctional benzoxazine monomers. The amines generally have from about 1 to about 40 carbon atoms unless they include aromatic rings and then they may have from about 6 to about 40 carbon atoms. The amine of di or polyfunctionality may also serve as a branch point to connect one polybenzoxazine to another.

The preferred phenolic compounds are diphenols (e.g. bisphenol-A), triphenols, etc., e.g. polyphenols, wherein each phenolic group in the phenolic compound has on average about 6 to about 20 carbon atoms per phenol group but can include monohydric phenols including substituted phenols such as cresol. The use of phenols with two or more hydroxyl groups reactive in forming benzoxazines may result in branched and/or crosslinked products. The groups connecting said phenolic groups into a phenol ($R_1$) can be branch points or connecting groups in the polybenzoxazine.

When n is 2, 3 or 4, examples of the $R_1$ connecting groups include but are not limited to

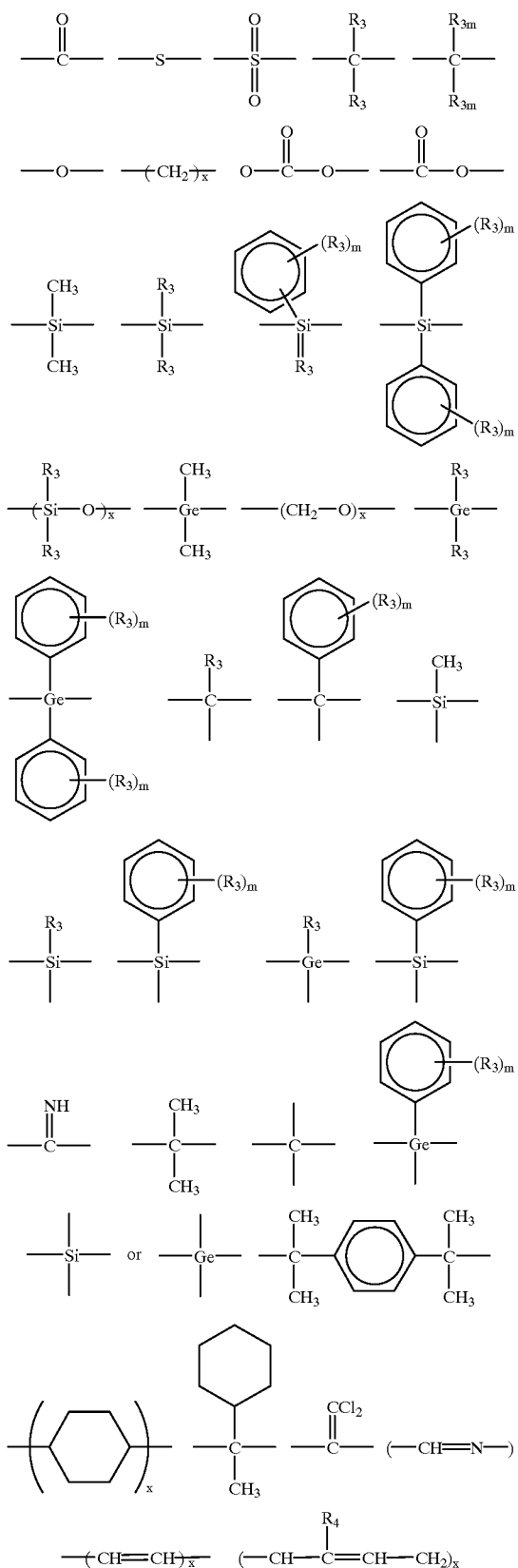

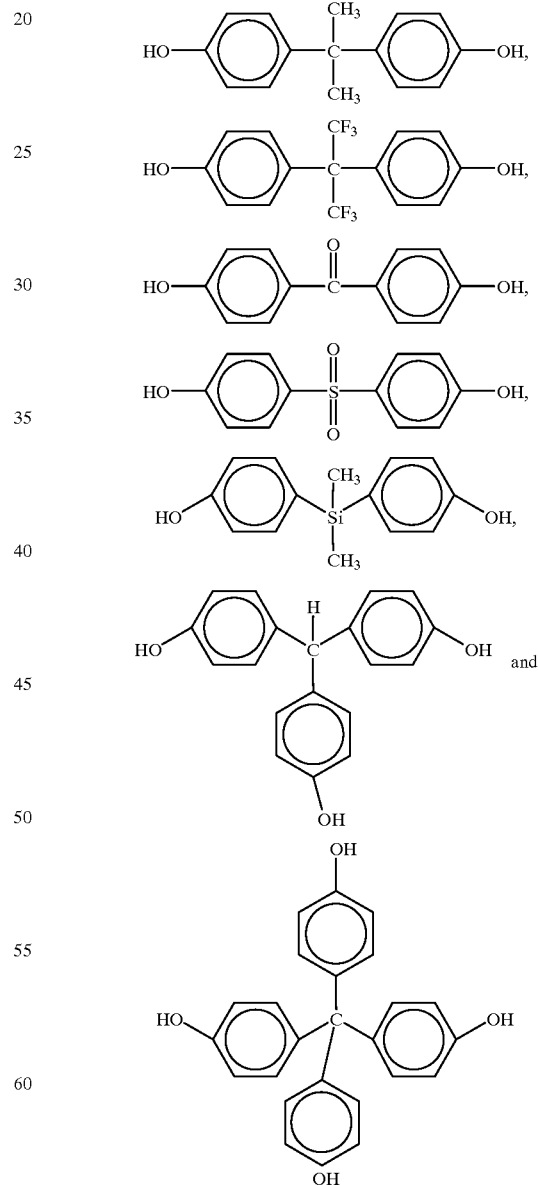

where x can vary from 1 to about 100. It may be desirable that $R_1$ be ortho, meta, or para to the oxygen atom of the benzoxazine monomer of Formula B. $R_4$ can be H, $CH_3$, or Cl such that the repeat unit is from butadiene, isoprene or chloroprene respectively.

The variable m can be an integer from 0 to 5 and $R_3$ can be H or $R_2$. Furthermore, each benzene ring, as shown by $(R_3)_m$ where m is an integer from 0 to 3 and $R_3$ is as defined later, can have more than one substituent of the same structure or a mixture of the $R_3$ structures. Preferably $R_3$ is not the amine or polyamine components of $R_2$. Preferably $R_3$ is an alkyl of 1 to 9 carbon atoms such as $CH_3$, $C_2H_5$, $C_3H_7$ or $C_4H_9$, or a mono or poly fluorinated alkyl of 1 to 9 carbon atoms such as $CF_3$, $C_2F_5$, $C_3F_7$. These $R_1$ compounds are well known to those familiar with phenolic compounds. Generally $R_1$ can be any of the known connecting groups that interconnect two or more phenols. Known connecting groups refers to those which are present in commercially available phenols, are in experimentally available phenols, and phenols whose synthesis are described in the published literature. Examples of such phenols include The aldehydes used to form the benzoxazine can be any aldehyde but preferably the aldehydes are those having from about 1 to about 10 carbon atoms with formaldehyde being highly preferred.

As is well known, benzoxazine monomers are made from the reaction of three reactants, aldehydes, phenols, and primary amines by procedures using a solvent or solventless systems. U.S. Pat. No. 5,543,516, hereby incorporated by reference, sets forth a generally solventless method of forming benzoxazine monomers. An article by Ning and Ishida in Journal of Polymer Science, Chemistry Edition, vol. 32, page 1121 (1994) sets forth a procedure using a solvent which can be used to prepare benzoxazine monomers. The procedure using solvents is generally common to the literature of benzoxazine monomers.

EXAMPLES

In the first study methyl groups, weak activators towards electrophilic aromatic substitution, were added as substituents groups to various sites on the aromatic amine groups. More strongly activating substituent groups, such as hydroxyl groups, are difficult though possible to incorporate due to the necessity of forming closed benzoxazine rings during the monomer synthesis. Adding a methyl or methoxy group to the para position of the aromatic amine should block the ring from reaction since the meta positions are unfavored for electrophilic substitution reactions due to the ortho/para directing nature of the nitrogen. Addition of a methyl group in the ortho position will likely decrease the activation of the open para position relative to the meta position and will serve to illustrate the effects of steric hindrance on the polymerization. Adding methyl groups to one or both meta positions should increase the activation of the para position enough to either compete with the traditional ortho position on the phenolic group for electrophilic substitution reactions or dominate and serve as the only site of reaction.

Monofunctional benzoxazine monomers were synthesized from 4-t-butyl-phenol (para substituted)(4TBUPH) or 2,4-dimethyl phenol (ortho and para substituted)(24DMP) with a series of aromatic amines. The para substituted phenol would be similar to bisphenol A and would have one available ortho position for polymerization with a Mannich bridge. The ortho and para substituted phenol would have no available ortho positions after forming a benzoxazine and thus a benzoxazine formed from this phenol should not be readily polymerizable. The aromatic amines include aniline, o-toluidine (ot), m-toluidine (mt), p-toluidine (pt), and 3,5-xylidine (35x). These represent nonsubstituted, ortho substituted, meta substituted, para substituted, and dimeta substituted aniline.

All the compounds were used as received from Aldrich Chemical Co. without further purification. The monofunctional benzoxazines were synthesized via a solventless method discussed in full detail in the Ph.D. Thesis of J. Liu from Case Western Reserve in 1995. The phenol, paraformaldehyde, and amine were added to an open container in stoichiometric amounts (1:2:1). The reactants were mixed for 20 minutes at 120° C. The crude reaction product was dissolved in diethyl ether and washed with 2N NaOH solution at least ten times and rinsed with deionized water. The purified products were dried over sodium sulfate and the solvent was removed under vacuum. The compounds were sequentially recrystallized from methanol twice and finally ethanol once. The residual ethanol was removed under vacuum at room temperature for 24 hours.

Benzoxazine monomers were prepared from the above reactants. They will be designated as the hyphenated combination of the abbreviations for the phenol and the aromatic amine. They include (24DMP-ot) a needle-like crystalline powder, (24DMP-mt) a light tan crystalline powder, (24DMP-pt) a white plate-like crystalline powder, (24DMP-35x) a white crystalline powder, (4TBUPH-a) a white crystalline powder, (4TBUPH-ot) a white needle-like crystalline powder, (4TBUPH-mt) a light tan crystalline powder, (4TBUPH-pt) a white plate-like crystalline powder, (4TBUPH-35x) a yellowish viscous liquid.

The benzoxazine monomers were reacted (e.g. hopefully polymerized) in NMR tubes with and without phenolic initiators under an argon atmosphere. The partially reacted materials were dissolved in deuterated chloroform and used for $^1$H and $^{13}$C NMR spectroscopy. The molecular weight of the resulting polymers was determined via size exclusion chromatography (SEC). The samples for molecular weight determination were prepared by diluting the NMR solution with HPLC grade tetrahydrofuran (THF).

2,4-dimethyl phenol-Based Monomers and Polymers

All of the 24DMP based benzoxazine monomers showed a distinct melting peak in the DSC analysis except for 24DMP-a, which was a viscous liquid at room temperature. A calorimetric analysis of the 24DMP based benzoxazines showed an exotherm which decreased as a function of the number of methyl substituents in the meta position of the arylamine ring increased i.e. benzoxazines from meta-toluidine had a lower temperature exotherm than benzoxazines from nonsubstituted aromatic amines and benzoxazines from 3,5-xylidine showed a still lower exotherm. Since benzoxazines from 24DMP are not believed to be ring opening polymerizable, the presence of a reaction exotherm in these materials is surprising. The low heats of reaction suggest that these exotherms may simply represent the ring opening and/or cleaving reactions. The results on benzoxazines from meta-toluidine and 3,5-xylidine may be due to polymerization to para activated positions on the arylamine ring or another side reaction.

After reaction of the 24DMP-based monomers under argon in the NMR tubes for 3 hours at 200° C., the molecular weight distribution was determined via SEC. The retention time of the monomer species is about 30.2 minutes. 24DMP-ot and 24DMP-pt showed only a small shoulder in the SEC plot at around 29.2 minutes which is typical for an open-ring monomeric species. This is consistent with the ortho-toluidine and para-toluidine not being reactive in electrophilic aromatic substitution reactions by the Mannich bridge from the oxazine ring opening and not forming dimers or oligomers. The 24DMP-mt showed peaks associated with the monomeric and open ring but additionally exhibits a peak centered at 28.4 minutes from a larger molecular weight species. The higher molecular weight species were also present in the 24DMP-35x. The higher molecular weight species are primarily dimeric in nature with smaller additional amount of higher oligomers such as trimers and tetramers. These dimers and oligomers are evidence that there is a reaction difference in the benzoxazines formed with para- directing substituents on the aromatic amine.

NMR analysis of the monomers after the polymerization basically confirmed the SEC analysis. It was observed that 24DMP-mt showed resonance at 4.27 ppm, which has been previously assigned to the open ring methylene protons of a Mannich base having the structure

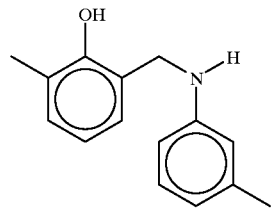

Another prominent resonance corresponding to a methylene proton of a open ring Schiff base can be observed at 8.52 ppm. It has the structure

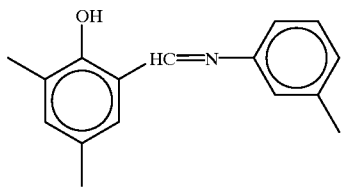

The oxazine rings of 24DMP-mt evidently started to open during the temperature regime employed, although a considerable amount of monomer remains after 3 hours. These open ring products participated in a cleavage reaction at this elevated temperature, which produces the Schiff base. Thus while the meta-toluidine is more active toward electrophilic para substitution reactions the meta substituent may lower the ring opening temperature allowing more side reactions to occur with meta-toluidine than with aniline, ortho-toluidine, or para-toluidine.

Blocking the preferred site of reaction on the phenol, i.e. the site ortho to the hydroxyl group, with a methyl substituent in 24DMP was effective in preventing the ring-opening polymerization from occurring in 24DMP-ot and 24DMP-pt. Activating the arylamine ring with methyl substituents at one or both meta positions facilitated the formation of the open-ring species at lower temperatures. The presence of methyl substituents in the meta positions must allow for sufficient electron density to be pushed into the oxazine ring, without the formation of more stable hyperconjugated resonance structures, such that the oxazine rings are less stable against ring opening.

Since higher molecular weight species were observed for 24DMP-mt and 24DMP-35x, it is necessary to determine if the site of reaction has simply shifted to the arylamine ring or if another polymerization/degradation reaction is taking place. Based on a $^1$H NMR resonance near 4.34 ppm associated with the methylene protons of the Mannich bridge, and the lack of open ortho and para positions on the phenol for addition of the Mannich bridge, it is assumed the reaction site for the Mannich bridge was shifted to the para position on the arylamine ring. This type of linkage will be referred to as an arylamine Mannich bridge.

The $^1$H NMR resonance assigned to the Mannich bridge methylene protons is small in 24DMP-35x suggesting that either few para sites on the arylamine ring have served as sites for polymerization or the para positions reacted with the Mannich bridges subsequently cleaving during the cure. Numerous resonances in the region of 3.7 to 3.9 ppm are greatly enhanced. A resonance at 3.85 ppm can be assigned to the formation of a bisphenolic methylene structure as shown below.

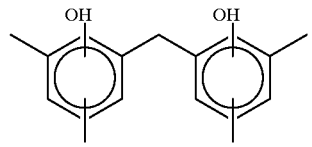

$^{13}$C NMR spectroscopy of 24DMP-mt and 24DMP-35x lacks any significant resonances at 79.3 and 50.2 ppm associated with the methylene carbons in the oxazine ring. This indicates near complete loss of the oxazine ring structure. The large resonance at 48.6 ppm in 24DMP-mt is assigned to the open ring Mannich base methine carbon. A resonance corresponding to the methylene carbon of the aromatic Schiff bass species mentioned previously is located at 162.5 ppm. In the case of 24DMT-mt a resonance corresponding to the phenolic Mannich bridge carbon appears near 49.0 ppm. A new resonance appeared at 54.7 ppm which can be assigned to the other carbon in the arylamine Mannich bridge which is attached to the para position on the arylamine ring, since the chemical shift is within 0.2 ppm of the value predicted by simple $^{13}$C chemical shift calculations.

A resonance appears near 30.5 ppm in both 24DMP-mt and 24DMP-35x. This resonance can be assigned to the methylene carbon in the bisphenolic methylene structure mentioned previously. The relative intensity of this peak between 24DMP-mt and 24DMP-35x agrees with the $^1$H NMR data. A second prominent resonance appears near 32.2 ppm. This is attributable to a methyl carbon in an N-methyl Mannich base species. A strong resonance near 29.1 ppm is assigned to a methylene carbon in a methylene bridge between an ortho position on a phenolic molecule and a position (presumably the activated para position) on the aromatic ring.

4-t-butyl phenol-Based Monomers

In order to determine if the ring-opening polymerizations of benzoxazine can occur with attachment to arylamine sites when there is a free ortho site on the phenolic ring concurrently available, a series of monomers based on 4-t-butyl phenol was synthesized. The t-butyl protecting group was selected to simulate the bulkiness of the isopropylene linkage of Bisphenol-A.

The DSC thermograms of the 4TBUPH-based benzoxazines are similar to those of the 24DMP-based benzoxazines. Addition of a methyl substituent on the meta position of the arylamine ring decreased the peak exotherm temperature and increases the heat of reaction. SEC was used to determine the molecular weight distribution of the oligomeric species after 190° C. for 2 hours and 200° C. for 1 hour (a typical step cure for difunctional benzoxazine resins). As with the 24DMP the molecular weight of the polymerized species increased as the para position of the arylamine ring is increasingly activated for electrophilic aromatic substitution reactions. It was observed that the 4TBUPH-ot monomer did not polymerize well which is probably due to thermal degradation. The low basicity of o-toluidine (ot) and steric hindrance around the amine may hinder polymerization.

1H NMR analysis indicated that the benzoxazine rings were not completely reacted (opened) even after an hour at 200° C. The 4TBUPH-mt monomer shows a distinguishing resonance at 3.85 ppm which corresponds to the methylene protons of the bisphenolic methylene species. This side reaction evidently occurs even when there are free ortho sites on the phenolic ring. It produces:

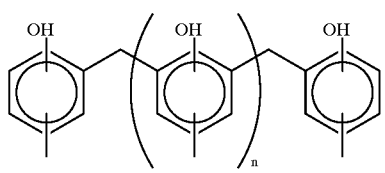

13C NMR analysis confirmed significant amounts of monomer remain for 4TBUPH-ot while almost none remains for 4TBUPH-mt. Around 30.8 ppm a small resonance appears in 4TBUPH-35x due to the formation of bisphenolic methylene linkages.

Bisphenol A Based Benzoxazines

Difunctional benzoxazines were synthesized via a solventless synthesis method discussed in J. Liu's Ph.D. thesis. The Bisphenol-A, paraformaldehyde, and arylamine were added to an open container in stoichiometric amounts (1:4:2). The reactants were mixed for 20 minutes at 120° C. The crude reaction products were dissolved in diethyl ether and washed with 2N NaOH solution and rinsed with deionized water. The purified products were dried over sodium sulfate and the solvent was removed under vacuum.

The benzoxazine monomers will be described by hyphenated abbreviations for the phenol and the aromatic amine used in their preparation. BA will be the abbreviation of Bisphenol A. The amines are aniline (a), o-toluidine (ot), m-toluidine (mt), p-toluidine (pt), and 3,5-xylidine (35x).

The BA-a was a white powder. The BA-ot was a white powder. The BA-mt was a light tan powder. The BA-pt was white crystalline powder. Due to the higher melting temperature of p-toluidine compared to the other amines, the monomer forming reaction was carried out at a higher temperature of 135° C. The BA-35x was a yellowish white powder.

The curing (polymerization) reaction for the benzoxazines was 140° C. for 30 min, 160° C. for 30 min, 170° C. for 45 min, 180° C. for 45 min, 190° C. for 75 min, and 200° C. for 90 min. The ring content before polymerization for the monomers was from about 83 to about 95% of the theoretical amount. FTIR analysis of the monomers with bands such as 1232 cm$^{-1}$ for asymmetric C—O—C stretch, 1030 cm$^{-1}$ characteristic of the —CH$_2$—O stretch of the aromatic ether and 947 cm$^{-1}$ associated with the —C—O—C cyclic acetal vibrational mode or a C—H out of plate deformation confirmed the formation of the benzoxazine rings.

The curing exotherms for most of the BA-based benzoxazines were not unusual except for BA-mt and BA-35x. The curing of BA-mt and BA-35x exhibited two peaks, one large narrow peak centered at 231 C and another small broad peak centered at 246. BA-35xt also exhibited peaks at 218 and 239 C. These two different peaks suggest reactions at two different sites, said reactions having different kinetics.

Cured samples of the different polybenzoxazines were filed down into flat, round disks and placed in hermetic aluminum pans. The temperature was ramped at 10° C./min under a nitrogen atmosphere. The thermal stability of the cured benzoxazines was measured by thermogravimetric analysis (TGA) using a TA Instruments Hi-Res 2950 Thermogravimetric Analyzer equipped with a Evolved Gas Analysis (EGA) furnace. The flow cell and transfer line were heated to 300° C. to prevent condensation of the evolved gases. FTIR spectra of the evolved gases were obtained on a Biorad FTS-60A FTIR Spectrometer.

BA-ot had the least stability with a 5% weight loss at 288° C. BA-a and BA-pt had a 5% weight loss at 315 and 305° C. respectively. The meta-substituted BA-mt and BA-35x possess the highest 5% weight loss temperature of 350° C. This is the highest 5% weight loss temperature reported for a neat Bisphenol-A based benzoxazines incorporating arylamines, without reactive substituent functionalities on the amine. The ultimate char yield at 800° C. of the 5 compounds are all similar at about 30–31%. This result is expected since no new chemical functionalities have been added. Only when the possibility of forming more stable cyclic structures is introduced will the char yield be significantly enhanced.

The glass transition temperatures of the various polymerized benzoxazines are BA-ot, 114; BA-a, 170; BA-pt, 158; BA-mt, 210; and BA-35x, 245° C.

Gases were also collected from the series of benzoxazines during degradation reactions and analyzed by GC/MS. For the traditional benzoxazine polymer the pendant arylamine group is the most easily volatilized upon cleavage of the Mannich bridge and therefore is the predominant species in the evolved gases. The BA-ot generated the most free amine species. For BA-mt the evolved amine was analyzed to find that both the activated 4 and 6 positions appear to have reacted. In the BA-35x, the 4 position dominated over the more sterically hindered 2 position.

The benzoxazine monomers and polymers disclosed herein would be useful as matrix resins in molding compounds, fiber reinforced boards for electronics, as adhesives or potting resins for electronic applications, as flame retardant adhesives or in flame retardant composites for airplanes and other transportation vehicles.

While in accordance with the patent statutes the best mode and preferred embodiment have been set forth, the scope of the invention is not limited thereto, but rather by the scope of the attached claims.

What is claimed is:

1. A benzoxazine monomer comprising the benzoxazine reaction product of at least one phenolic compound, at least one aldehyde, and either a) at least one aromatic amine, said aromatic amine having at least one meta substituent which activates the aromatic ring for electrophilic aromatic substitution at the para position or b) a naphthenic amine having a substituent which activates the aryl ring for electrophilic aromatic substitution on one or more of the $5^{th}$ through $8^{th}$ carbon atoms of the naphthalene, or combinations of a) and b).

2. A monomer according to claim 1, wherein at least 10 mole percent of the total amine reacted into said benzoxazine monomer is said aromatic amine with at least one meta substituent that activates the ring for electrophilic substitution at the para position.

3. A monomer according to claim 1, wherein at least 50 mole percent of the total amines reacted into said benzoxazine monomer is said aromatic amine with at least one meta substituent that activates the ring for electrophilic substitution at the para position.

4. A monomer according to claim 2, wherein said 10 mole percent of said total amines is one or more mono or di substituted aniline molecules having meta substituent(s) which are independently an alkyl group of 1 to 4 carbon atoms or alkoxy group of 1 to 4 carbon atoms or combinations thereof.

5. A monomer according to claim 3, wherein said 50 mole percent of said total amines is one or more mono or disubstituted aniline molecules having meta substituent(s) which are independently an alkyl group of 1 to 4 carbon atoms or alkoxy group of 1 to 4 carbon atoms.

6. A monomer according to claim 4, wherein at least 10 mole percent of the total phenolic compound reacted into said benzoxazine monomer comprises a di or polyhydric phenol characterized by having at least two aromatic hydroxyl groups that can form oxazine rings with formaldehyde and aniline under conventional reaction conditions for benzoxazine.

7. A monomer according to claim 2, further including benzoxazine monomers wherein the amine component of said benzoxazine is other than said aromatic or naphthenic amine.

8. A polymer comprising the ring opening polymerization reaction product of benzoxazine monomer, said monomer derived from the benzoxazine ring forming reaction of at least one phenolic compound, at least one aldehyde, and either at least one a) aromatic amine having one or more meta substituents that activate the aromatic ring for electrophilic aromatic substitution at the para position or b) a naphthenic amine having a substituent that activates the aryl ring for electrophilic aromatic substitution on one or more of the $5^{th}$ through $8^{th}$ carbon atom of the naphthalene, or combinations of a) and b).

9. A polymer according to claim 8, wherein said at least one meta substituent comprises at least one alkyl of 1 to 4 carbon atoms and/or at least one alkoxy of 1 to 4 carbon atoms.

10. A polymer according to claim 9, wherein said at least one meta substituted aromatic amine comprises 3-toluidine or 3,5-xylidine.

11. A polymer according to claim 8, further including Mannich bridge attachments to the para position on the benzene ring of said aromatic amine or methylene bridge attachments between an ortho position carbon of a phenolic molecule and a para position carbon on the benzene ring of said aromatic amine.

12. A polymer according to claim 8, further including methylene bridge attachments to the para postion of the benzene ring of said aromatic amine.

13. A polymer according to claim 8, wherein at least 10 mole percent of the total amine reacted into said benzoxazine monomer is said aromatic amine with at least one meta substituent that activates the ring for electrophilic substitution at the para position.

14. A polymer according to claim 12, further including repeating units from benzoxazine monomer(s) made from amines other than said aromatic amine.

15. In a process for forming a benzoxazine polymer including the steps of;
  a) reacting at least one phenolic compound, at least one aldehyde, and at least one 1) aromatic amine or 2) naphthenic amine to form at least one compound with one or more benzoxazine rings
  b) via a ring opening polymerization of said at least one compound forming a benzoxazine polymer
  the improvement wherein said aromatic amine has at least one meta substituent which activates the aromatic amine for electrophilic substitution at the para position or said naphthenic amine has either 1) one or more alkyl substituents or 2) one or more alkoxy substituents on the $5^{th}$ through $8^{th}$ carbon atom of the naphthalene or combinations thereof.

16. A process according to claim 15, wherein said aromatic amine is mono-meta or di-meta substituted.

17. A process according to claim 15, wherein said aromatic amine with at least one meta substituent is at least 10 mole percent of the total amines used to form said compound with one or more benzoxazine rings.

18. A process according to claim 15, wherein said aromatic amine is 3-toluidine or 3,5-xylidine.

19. A process according to claim 15, wherein at least 50 mole percent of said phenolic compound is a diphenol or polyfunctional phenol.

* * * * *